United States Patent
Fleig et al.

(10) Patent No.: US 11,478,168 B2
(45) Date of Patent: *Oct. 25, 2022

(54) DETERMINING A RANGE OF MOTION OF AN ARTIFICIAL KNEE JOINT

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventors: Oliver Fleig, Baldham (DE); Christian Brack, Neusaess (DE); Zohar Leder, Munich (DE); Martin Bauer, Munich (DE)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 17/395,163

(22) Filed: Aug. 5, 2021

(65) Prior Publication Data
US 2021/0361191 A1 Nov. 25, 2021

Related U.S. Application Data

(63) Continuation of application No. 17/068,401, filed on Oct. 12, 2020, which is a continuation of application
(Continued)

(51) Int. Cl.
*A61B 5/11* (2006.01)
*A61B 34/20* (2016.01)
(Continued)

(52) U.S. Cl.
CPC .......... *A61B 5/1121* (2013.01); *A61B 5/1072* (2013.01); *A61B 5/4585* (2013.01);
(Continued)

(58) Field of Classification Search
CPC ... A61B 19/5212; A61B 19/54; A61B 5/1121; A61B 19/50; A61B 2019/547;
(Continued)

(56) References Cited

U.S. PATENT DOCUMENTS 9,101,394 B2   8/2015  Arata et al.
2004/0019382 A1*  1/2004  Amirouche .......... A61B 5/4528
                                         623/20.14
(Continued)

FOREIGN PATENT DOCUMENTS

DE   102006056399 A1   5/2007

OTHER PUBLICATIONS

Thompson et al. "Biomechanical Effects of Total Knee Arthroplasty Component Malrotation: A Computational Simulation". Journal of Orthopaedic Research. Jul. 2011, p. 969-975 (Year: 2011).*

(Continued)

*Primary Examiner* — Amelie R Davis
*Assistant Examiner* — Helene Bor
(74) *Attorney, Agent, or Firm* — DLA Piper LLP

(57) ABSTRACT

A data processing method for determining a range of motion of an artificial knee joint which connects a femur and a tibia via a medial ligament and a lateral ligament, wherein at least the femur comprises an implant which forms a medial condyle and a lateral condyle, the method comprising the steps of: acquiring the maximum lengths of the lateral ligament and the medial ligament for a particular flexion angle of the knee joint; calculating a first virtual position between the femur and the tibia in which the lateral condyle of the femoral implant touches the tibia and the medial ligament is stretched to its maximum length; calculating a maximum valgus angle of the range of motion from the first virtual position; calculating a second virtual position between the femur and the tibia in which the medial condyle (Continued)

Figure 1:
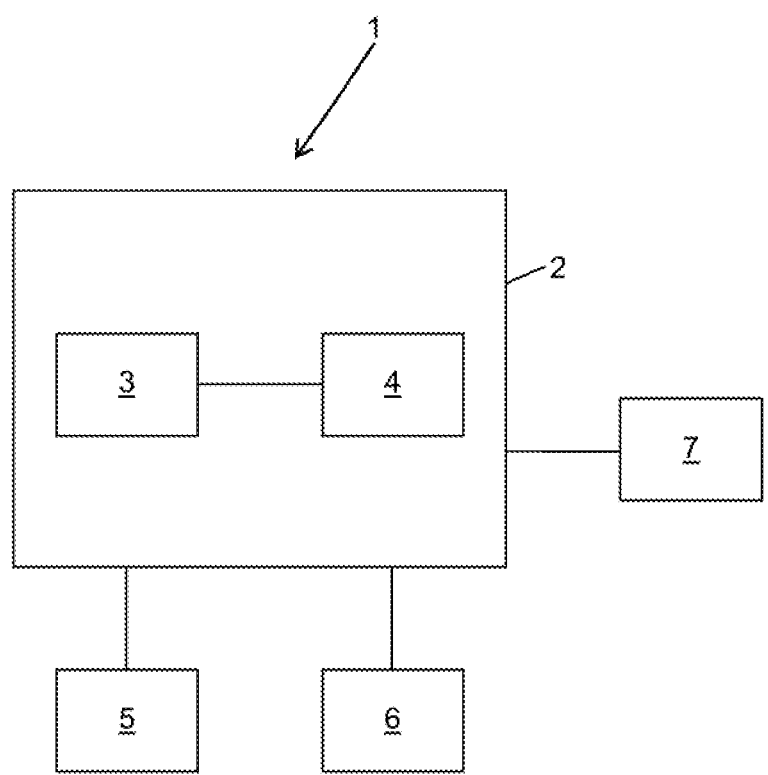

of the femoral implant touches the tibia and the lateral ligament is stretched to its maximum length; and calculating a maximum yarns angle of the range of motion from the second virtual position.

25 Claims, 12 Drawing Sheets

Related U.S. Application Data

No. 15/794,754, filed on Oct. 26, 2017, now Pat. No. 10,813,574, which is a continuation of application No. 14/405,427, filed as application No. PCT/EP2012/061188 on Jun. 13, 2012, now abandoned.

(51) Int. Cl.
*A61B 90/00* (2016.01)
*A61B 34/10* (2016.01)
*A61B 5/107* (2006.01)
*A61B 5/00* (2006.01)

(52) U.S. Cl.
CPC .............. *A61B 34/10* (2016.02); *A61B 34/20* (2016.02); *A61B 90/361* (2016.02); *A61B 90/39* (2016.02); *A61B 2034/104* (2016.02); *A61B 2034/2055* (2016.02); *A61B 2090/397* (2016.02)

(58) Field of Classification Search
CPC ............ A61B 2019/464; A61B 17/154; A61B 19/5244; A61B 5/4533; A61B 5/4528; A61B 2/3859; A61B 2019/502; A61B 2019/505; A61B 34/10; A61B 2090/397; A61B 34/20; A61B 90/361; A61B 90/39; A61B 5/1072; A61B 5/4585; A61B 2034/104; A61B 2034/2055
See application file for complete search history.

(56) References Cited

U.S. PATENT DOCUMENTS

| | | | |
|---|---|---|---|
| 2004/0254771 | A1 | 12/2004 | Riener et al. |
| 2005/0101966 | A1* | 5/2005 | Lavallee ................. A61B 5/062 623/20.14 |
| 2005/0119661 | A1* | 6/2005 | Hodgson ................. A61B 90/36 623/908 |
| 2005/0234332 | A1* | 10/2005 | Murphy ................. A61B 34/20 600/426 |
| 2005/0251148 | A1* | 11/2005 | Friedrich ............. A61B 17/155 606/88 |
| 2006/0161051 | A1 | 7/2006 | Terrill-Grisoni et al. |
| 2007/0179626 | A1 | 8/2007 | de la Barrera et al. |
| 2008/0243127 | A1 | 10/2008 | Lang et al. |
| 2008/0262812 | A1* | 10/2008 | Arata ..................... A61B 90/36 703/11 |
| 2010/0049195 | A1 | 2/2010 | Park et al. |
| 2014/0324403 | A1* | 10/2014 | Gotte ........................ A61F 2/46 703/2 |
| 2018/0296133 | A1 | 10/2018 | Brack et al. |

OTHER PUBLICATIONS

Walde et al. "Optimized Functional Femoral Rotation in navigated Total knee Arthroplasty Considering Ligament Tension" The Knee, vol. 17, No. 6, Dec. 1, 2010, pp. 381-386.
International Search Report and Written Opinion for International Application No. PCT/EP2012/061188 dated Mar. 11, 2013.
Van der Esch, et al., "Knee Varus-Valgus Motion During Gait—a Measure of Joint Stability in Patients with Osteoartritis?" Osteoarthritis and Cartilage, Vo. 16, No. 4, Mar. 29, 2008, pp. 522-526.

* cited by examiner

DETERMINING A RANGE OF MOTION OF AN ARTIFICIAL KNEE JOINT

The present application is a continuation of U.S. patent application Ser. No. 17/068,401, filed Oct. 12, 2020, which is a continuation of U.S. patent application Ser. No. 15/794,754, filed Oct. 26, 2017, now U.S. Pat. No. 10,813,574 issued Oct. 27, 2020, which is a continuation of U.S. patent application Ser. No. 14/405,427, filed Dec. 4, 2014, now abandoned, which is a U.S. national stage filing under 35 U.S.C. § 371 of International PCT Application No. PCT/EP2012/061188, filed Jun. 13, 2012, the content of each earlier application being incorporated by reference in its entirety in the present application.

The present invention relates to a data processing method, a computer program, a computer and a medical navigation system for determining a range of motion of an artificial knee joint.

A knee joint connects a femur and a tibia. One characteristic for describing the knee joint is its range of motion. In this document, "range of motion" means the range between the maximum varus angle and the maximum valgus angle for a particular flexion angle between the femur and the tibia. In other words, the range of motion describes the maximum tilt between the femur and the tibia in the coronal plane. The range of motion can optionally be given for a plurality of flexion angles, thus resulting in an envelope which describes the maximum varus/valgus angle over the range of flexion angles.

The range of motion is of particular interest in the case of an artificial knee joint, where the range of motion refers to the post-operative range of motion. In an artificial knee joint, at least the femur comprises an implant at its distal end. The implant forms a medial and a lateral condyle, thus recreating the original bone. Typically, the proximal end of the tibia is cut off. This cut is defined by a cutting plane. A tibial implant is typically, though not necessarily, placed onto the tibial cut.

Where a "bone" is mentioned in this document, this may refer to the bone itself or any implant attached (or to be attached) to the bone. The expression "femur" therefore relates to the femur alone or to a combination of the femur and a femoral implant, and the expression "tibia" may refer to the tibia alone or to a combination of the tibia and a tibial implant.

The aim of a total knee arthroplasty is to achieve a proper functionality of the artificial knee joint. This is assessed on the basis of the post-operative range of motion. It is therefore an object of the present invention to determine the range of motion before the arthroplasty is actually performed. "Determining" thus has the meaning here of "simulating" or "predicting". From this (predicted) post-operative range of motion, it is possible to determine whether or not the parameters, such as the selected implant(s) or the position or positions, are correct and will lead to a desired result.

The present invention relates to a method for determining a range of motion of an artificial knee joint which connects a femur and a tibia via a medial ligament and a lateral ligament, wherein at least the femur comprises an implant which forms a medial condyle and a lateral condyle. The method comprises the step of acquiring the maximum lengths of the lateral ligament and the medial ligament for a particular flexion angle of the knee joint. The maximum length of a ligament is the maximum length to which the ligament can be stretched, in particular without causing damage to the ligament.

The method also comprises the step of calculating a first virtual position between the femur and the tibia in which the lateral condyle of the femoral implant touches the tibia and the medial ligament is stretched to its full length. This first virtual position depends on the structure of the femoral implant, the position of the femoral implant on the femur, the maximum length of the medial ligament and the shape of the tibia (including, where applicable, a tibial implant). The next step then relates to calculating a maximum valgus angle of the range of motion from the first virtual position.

The method also comprises the step of calculating a second virtual position between the femur and the tibia in which the medial condyle of the femoral implant touches the tibia and the lateral ligament is stretched to its maximum length and the step of calculating a maximum varus angle of the range of motion from the second virtual position. These two steps are analogous to the steps of calculating the first virtual position and the maximum valgus angle, but relate to the knee joint being bent outwards rather than inwards.

Preferably, the internal external rotation, the anterior/posterior location and the lateral location are identical fir the first and second virtual positions. The flexion angle is necessarily identical for the first and second virtual positions. Within this document, the term "position" means the spatial location in up to three translational dimensions and/or the rotational alignment in up to three rotational dimensions.

Given the maximum varus and valgus angles, the range of motion of the artificial knee joint for the particular flexion angle is known. The process of determining the range of motion, or at least one of the maximum varus angle and maximum valgus angle, of the artificial knee joint can be repeated for a plurality of flexion angles in order to obtain an envelope of the range of motion over a range of flexion angles.

Within the scope of the present invention, the acquiring step does not involve manipulating a body in any way but rather merely receiving data, in particular maximum length datasets which represent the maximum length of the lateral ligament and the medial ligament. The present invention can however also comprise non-surgical procedures for measuring the maximum length.

The expression "acquiring data" encompasses in particular the scenario (within the framework of a data processing method) in which the data are determined by the data processing method or program. Determining data in particular encompasses measuring physical quantities and transforming the measured values into data, in particular digital data, and/or computing the data by means of a computer, in particular by computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.), or via the interface (for instance, from another computer or a network). The data can be made "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain an for provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably referred to as "XY information".

Within the anatomy of a knee joint, a ligament connects to the femur at a defined point and to the tibia at a defined point. Due to the shape of the bones, in particular the tibia, a ligament might not be straight. It can therefore be advantageous to not consider the actual length of the ligament, but to instead define the length of a ligament as the distance between the point on the femur at which the ligament connects to the femur and a plane defined with respect to the tibia. This plane which is defined with respect to the tibia is preferably the tibial cutting plane. This tibial cutting plane is either a planned (virtual) cutting plane or the plane of a cut which has been performed before the method according to the present invention is carried out and which does not form part of the present invention. A tibial cutting plane is typically, though not necessarily, perpendicular to the mechanical axis of the tibia and therefore a transverse plane.

In one embodiment of the invention, calculating a virtual position includes the step of calculating a virtual contact position in which both the lateral condyle and the medial condyle of the femur touch the tibia and the step of rotating the femur about the contact point between one of the condyles and the tibia until the opposing ligament is stretched to its maximum length. The opposing ligament with respect to the lateral condyle is the medial ligament and the opposing ligament with respect to the medial condyle is the lateral ligament. This approach starts from a stable virtual contact position in which both condyles are in contact with the tibia without penetrating into the tibia. The femur is then rotated about one of the contact points as far as the opposing ligament permits, thus resulting in the maximum possible varus or valgus angle.

In one embodiment, calculating the virtual contact position comprises the step of rotating the femur until its condyles have the same distance from the tibia (or, preferably, from the tibial cutting plane) and the step of moving the femur translationally relative to the tibia until both the condyles of the femur touch the tibia, i.e. the femur and the tibia are first aligned and then brought into contact.

As outlined above, the maximum length of a ligament is determined from a relative position between the femur and the tibia in which the ligament is stretched to its maximum length. Since the feature point on the femur at which the ligament connects is known, the position of this point, in particular relative to the tibia, is also known or can be determined. In another embodiment of the invention, a (first or second) virtual position is calculated by rotating the femur about said point until the condyle opposite the stretched ligament touches the tibia. This approach is complementary to the previously described approach in which a contact point is first determined and a rotation is then performed until a ligament is fully stretched.

In one embodiment of the present invention, a surface model of the femur and preferably also of the tibia is used for the calculating steps. The calculating steps comprise calculating a virtual position or a virtual contact position. A surface model of a bone represents the three-dimensional structure of the surface of the bone, for example as a grid model or a three-dimensional image dataset. Within this approach, collision techniques can be used in order to determine whether or not the femur and the tibia are in contact. A surface model of the tibia (or the tibial implant) or a plane defined in relation to the tibia can be used in the calculating steps.

As an alternative to using a surface model of the femur, the femur can also be described mathematically. The condyles of the femur in particular can be described mathematically because they are in contact with the tibia. The condyles of the femur are preferably modelled by a mathematical function and preferably as ellipses. Within this approach, geometrical methods can be used to calculate the contact position in which at least one condyle of the femur touches the tibia.

Not only the pivotal point but also an axis of rotation is required in order to define a rotation. Preferably, the axis of rotation is parallel to a cutting plane of the tibia (either a planned cutting plane or an actual cutting plane) and lies within the sagittal plane of the tibia. The axis of rotation is also deemed to be parallel to the cutting plane if the axis of rotation lies within the cutting plane. With such an axis of rotation, the rotation does not change the internal/external angle or the flexion angle.

In one embodiment, the maximum length of a ligament is calculated from a transformation matrix which represents a relative position between the femur and the tibia in which the ligament is stretched to its maximum length. This transformation matrix represents all the degrees of freedom (up to three rotational and/or up to three translational degrees of freedom) of the relative position and is for example a homogeneous 4×4 matrix. Homogeneous matrices are used to unify the calculations of three-dimensional rotations and translations in a four-dimensional space. This matrix can be determined by observing marker devices which are attached to at least one of the bones, preferably with one marker device attached to each bone, wherein a bone is registered to the marker device attached to it. It should be noted that the process of attaching a marker device to a bone or of registering a bone to a marker device, for example using a pointer, is not part of the present invention, but is performed before the range of motion is determined.

It is the function of a marker to be detected by a marker detection device (for example, a camera or an ultrasound receiver or analytical devices such as CTs or MRIs), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic-shape.

A marker device can for example be a reference star or a pointer or one marker or a plurality of (individual) markers which are preferably in a predetermined spatial relationship. A marker device comprises one, two, three or more markers, wherein if there are two or more markers, these are in a predetermined spatial relationship. This predetermined spatial relationship is in particular known to a navigation system and for example stored in a computer of the navigation system.

Merely for informational purposes, two possible approaches for ensuring that a ligament is stretched to its maximum length are described here. In the first approach, a varus or valgus stress is applied to the knee joint, for example by exerting an external lateral force on the knee, such that the ligament is fully stretched. This is performed once with a varus stress for acquiring a transformation matrix which represents a fully stretched lateral ligament and once with a valgus stress for acquiring a transformation matrix which represents a fully stretched medial ligament. If the range of motion is to be determined for a plurality of flexion angles, it is preferable to sample a plurality of transformation matrices by applying a lateral (varus or valgus) stress to the knee joint and bending the knee over a range of flexion angles while taking the transformation matrix samples.

In a second approach, a spreading device is inserted into the knee joint and adjusted such that both ligaments are fully stretched. In this case, a single transformation matrix is sufficient to calculate the maximum length of both the medial and the lateral ligament. As in the first approach, the knee can be bent over a range of flexion angles in order to determine a plurality of transformation matrix samples and so obtain an envelope of the range of motion.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable. In particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The method in accordance with the invention is in particular a data processing method. The data processing method is preferably performed using technical means, in particular a computer. The data processing method is in particular executed by or on the computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing" which describes computation, software, data access and storage services which do not require the end user to know the physical location and/or configuration of the computer delivering a specific service. In particular, the term "cloud" is used as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) such as is provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer.

The present invention also relates to a medical navigation system comprising a computer as described above and at least one of a stereoscopic camera and an electromagnetic receiver. The stereoscopic camera or the electromagnetic receiver is used to ascertain the position of a marker device attached to a bone. A stereoscopic camera captures a three-dimensional image from which the position of the marker relative to the camera can be calculated. An electromagnetic receiver receives electromagnetic radiation emitted from a marker device attached to a bone. The position of the marker device relative to the electromagnetic receiver can be calculated from the received electromagnetic signal.

It is within the scope of the present invention to combine one or more features of two or more embodiments, where technically feasible, to form another embodiment. It is also within the scope of the present invention to omit features which are not essential to implementing the inventive concept or to replace such a feature with another feature, in particular a feature exhibiting a similar function.

Figure 2:
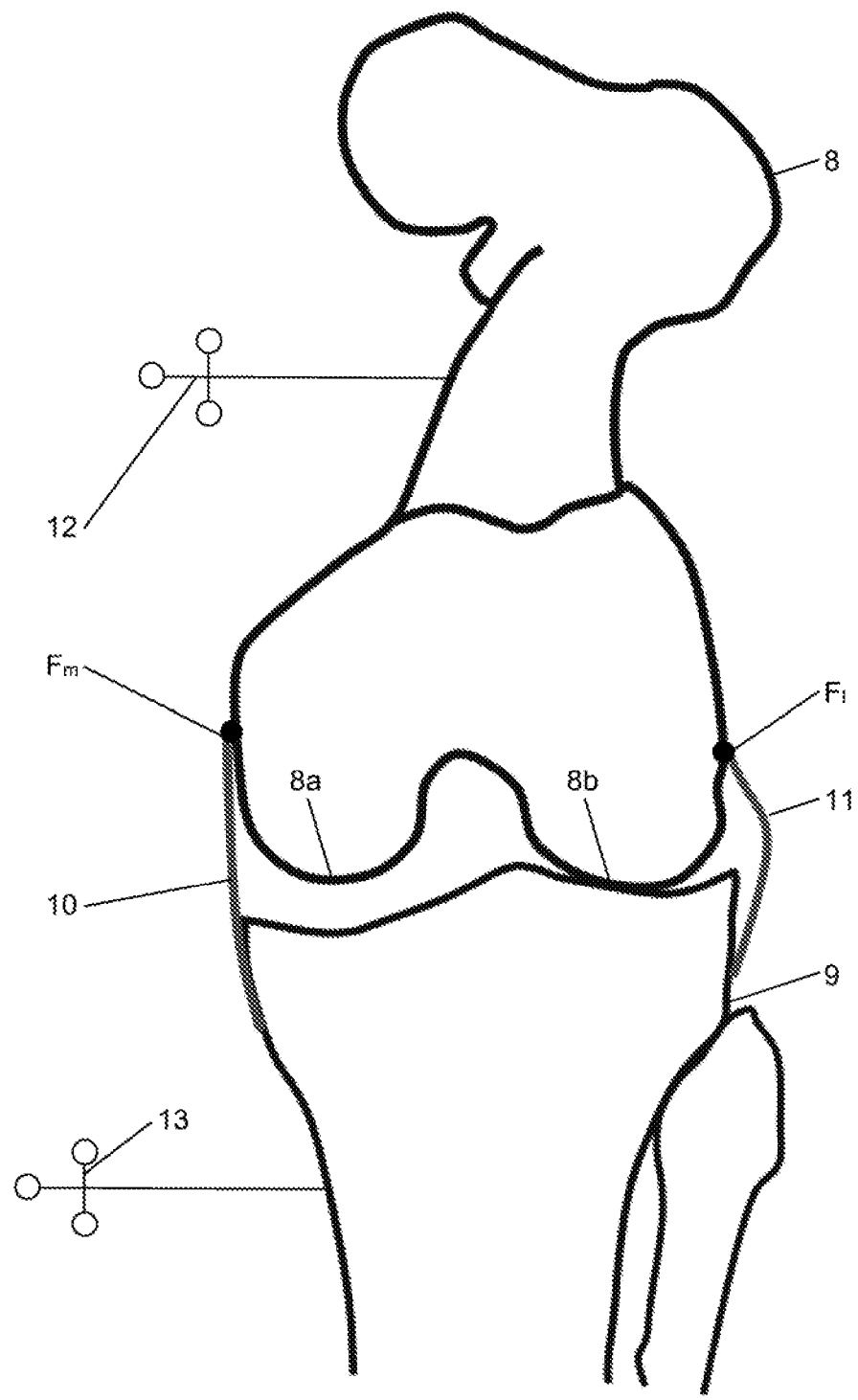
Figure 3:
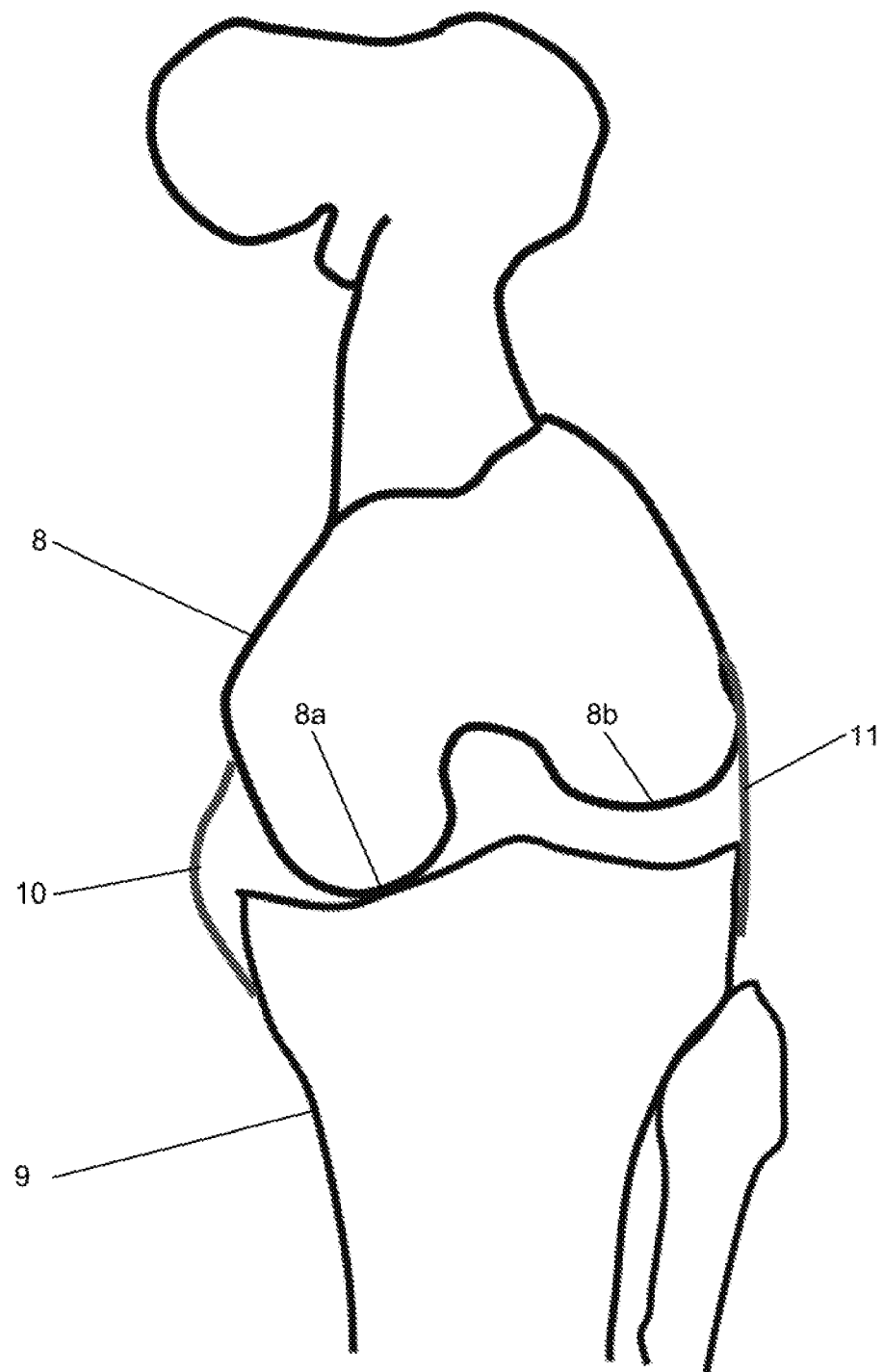
Figure 4:
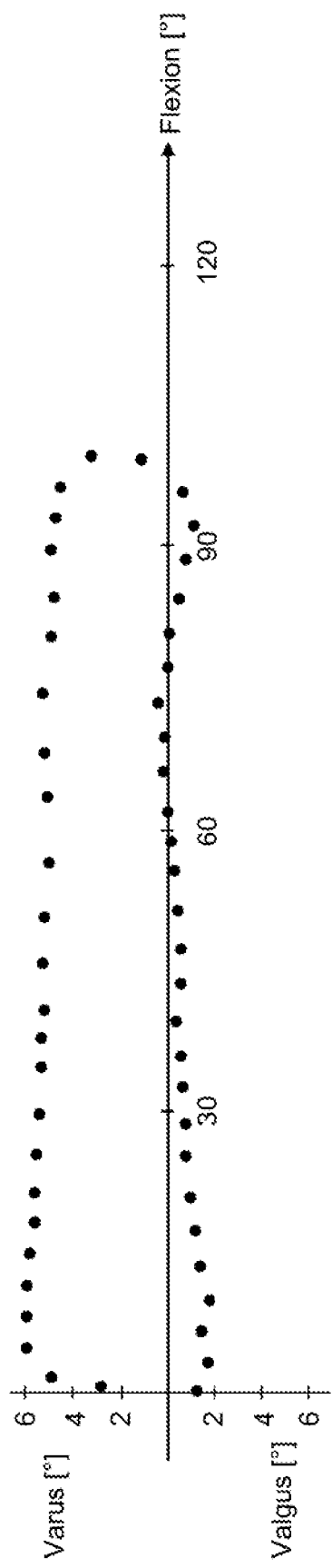
Figure 5B:
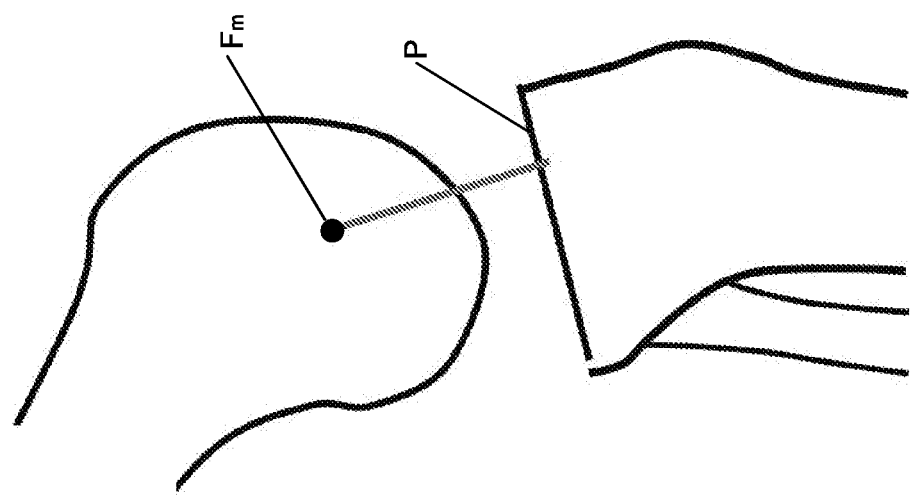
Figure 5A:
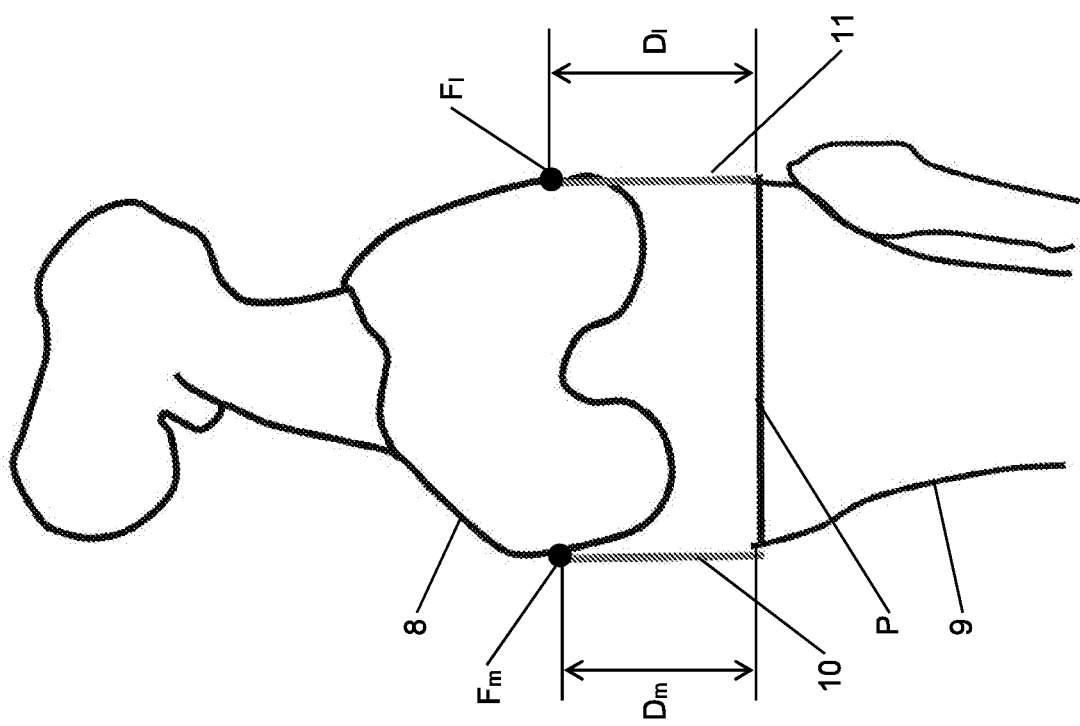
Figure 6:
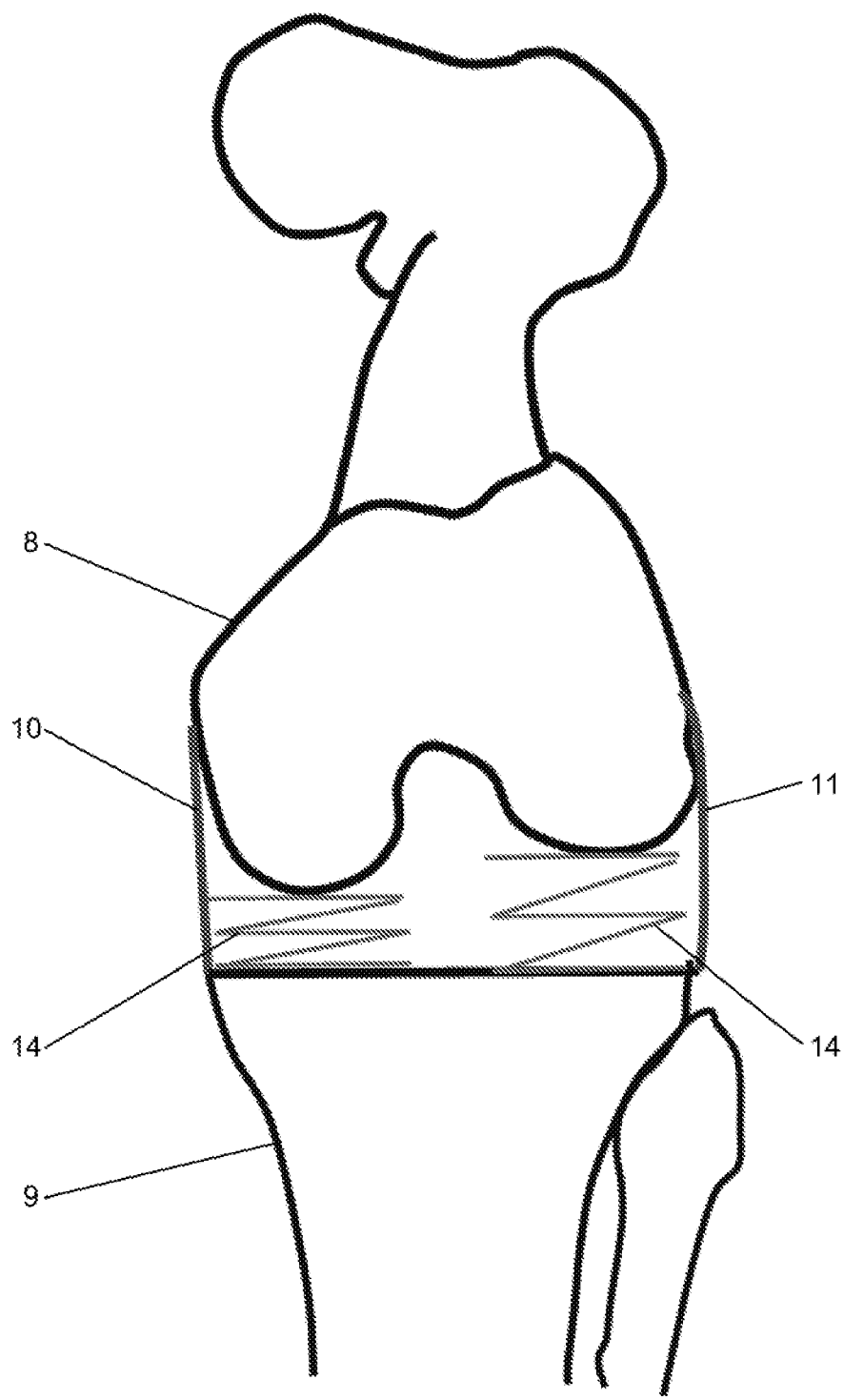
Figure 7:
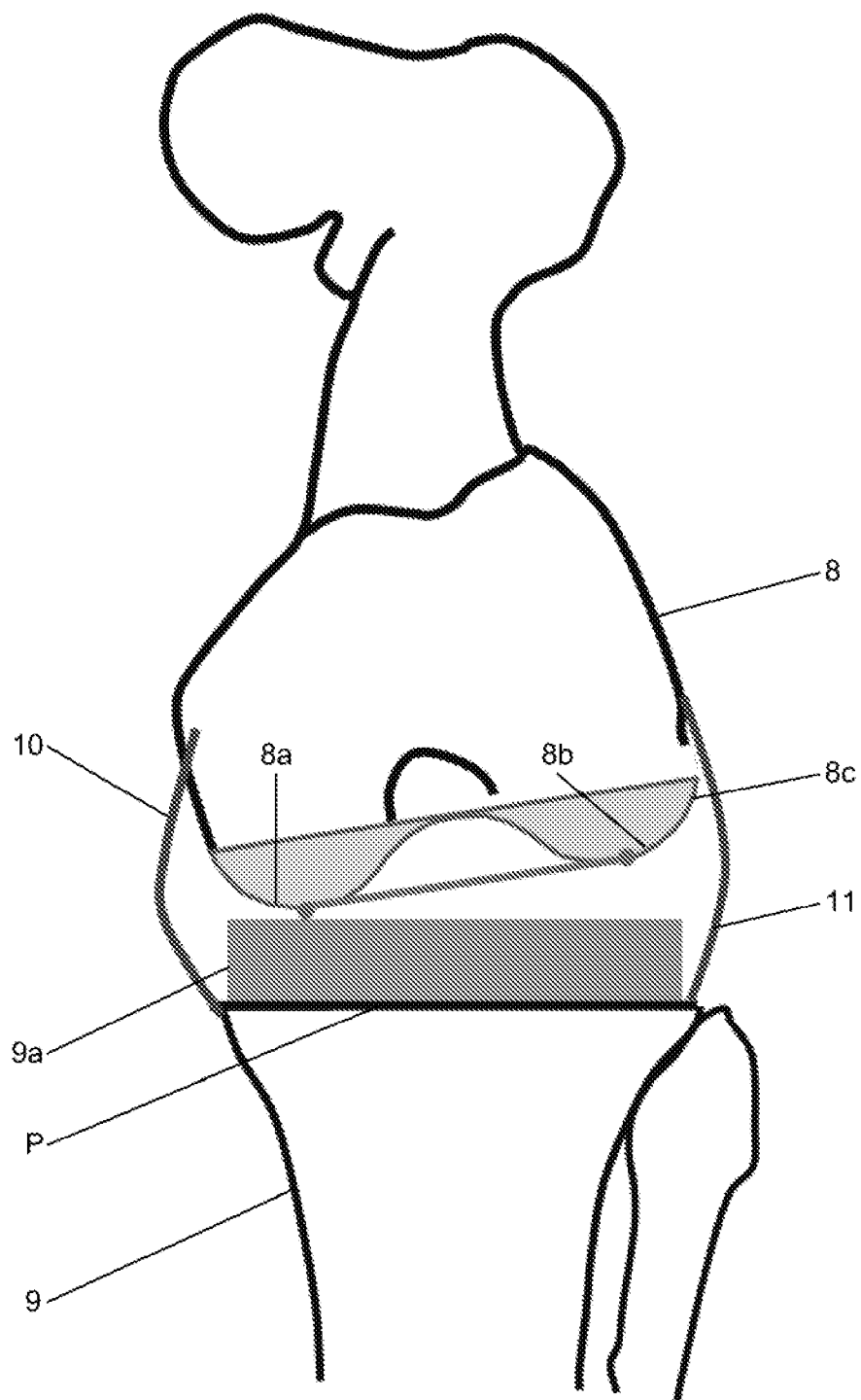
Figure 8:
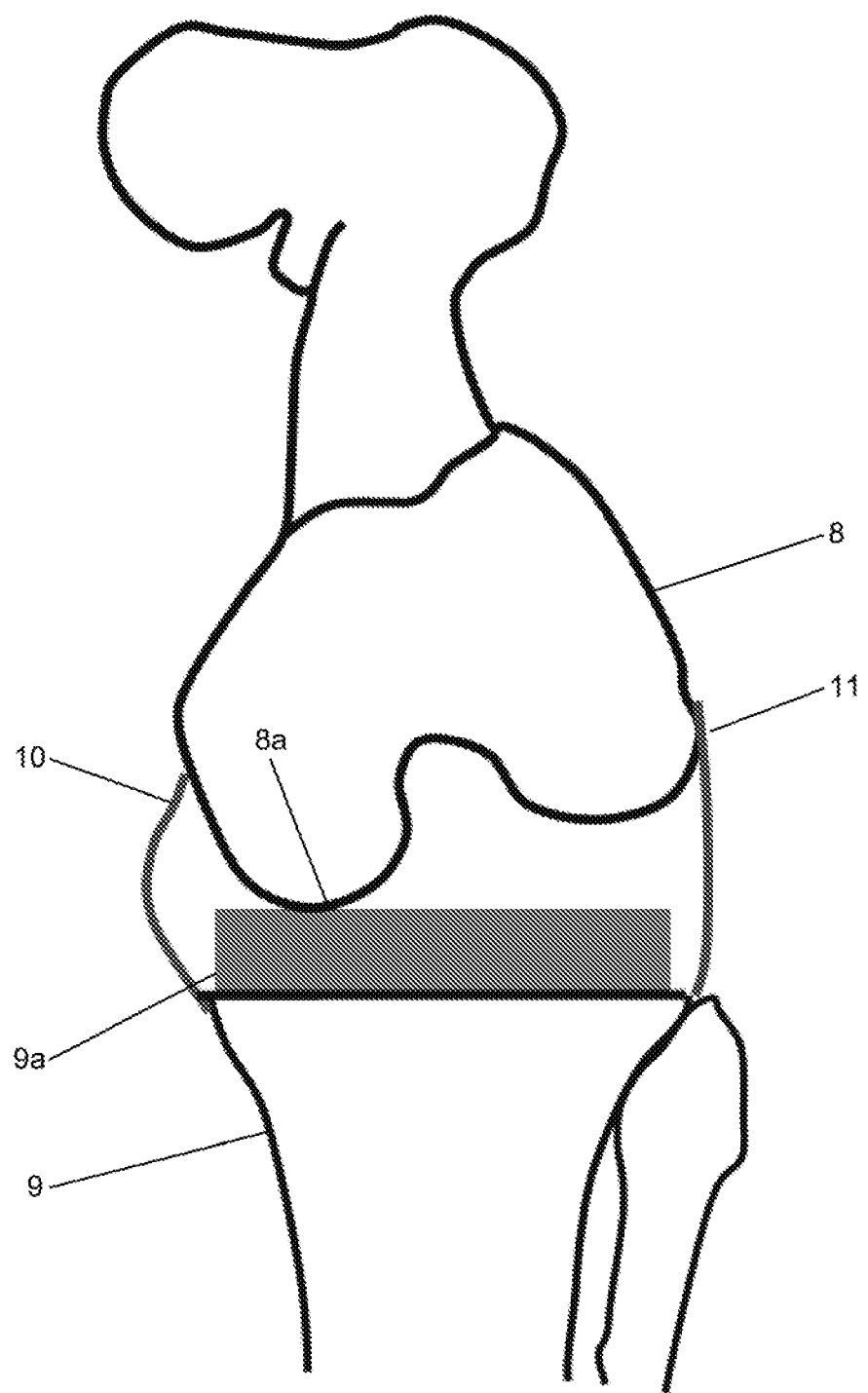
Figure 9:
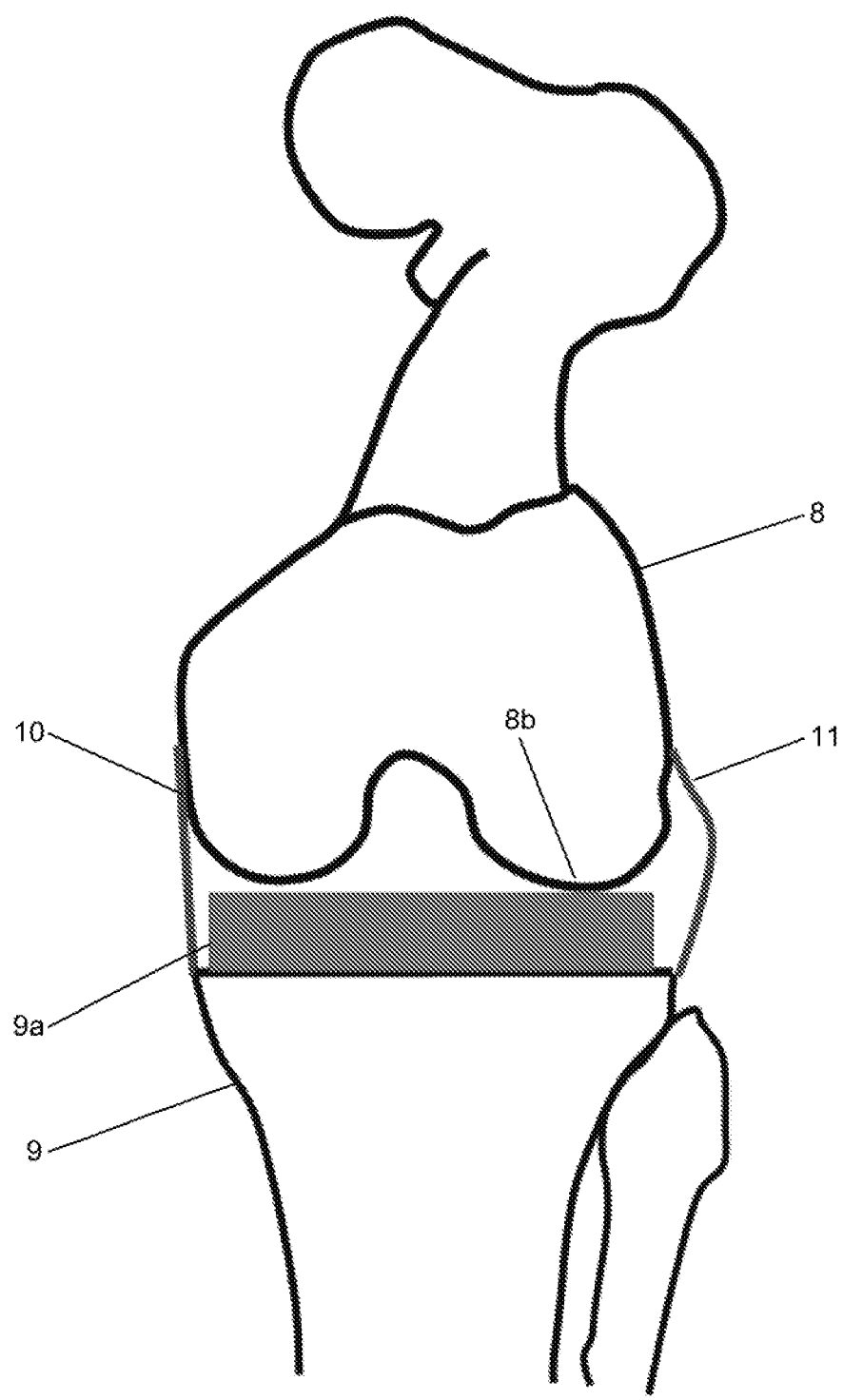
Figure 10:
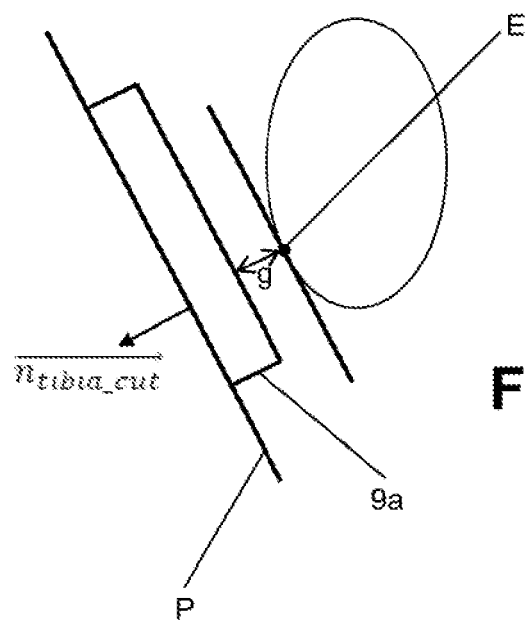
Figure 11:
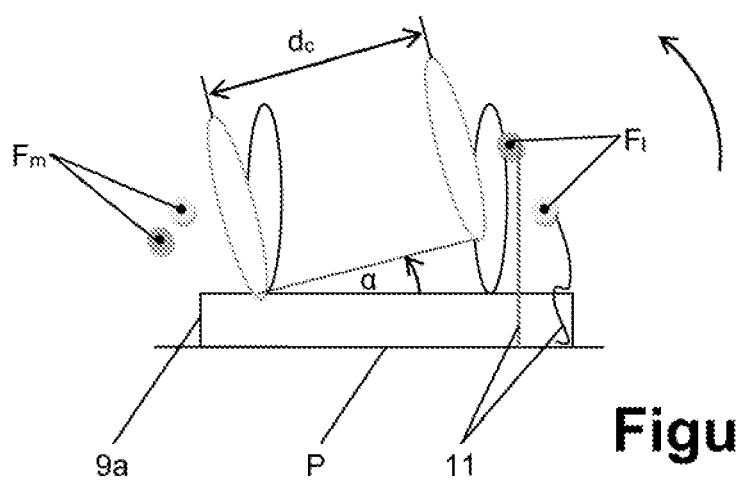
Figure 12:
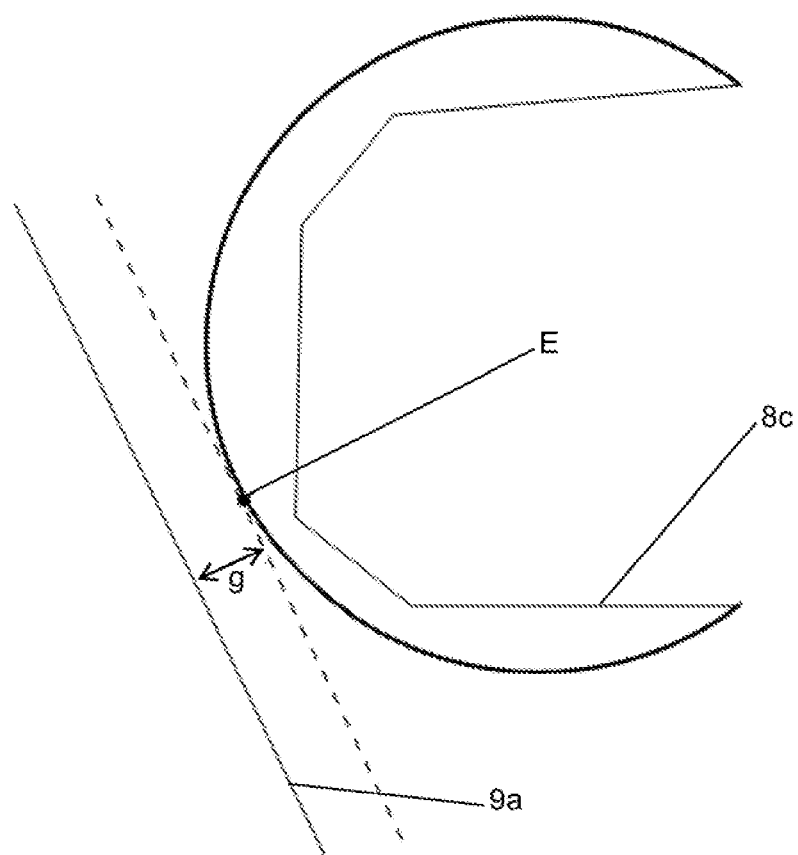

The invention shall now be explained in more detail with reference to the accompanying figures, which show:

FIG. 1 a medical navigation system for carrying out the invention;

FIG. 2 a pre-operative knee joint, with the medial ligament stretched;

FIG. 3 the knee joint of FIG. 2, with the lateral ligament stretched;

FIG. 4 an envelope of the pre-operative range of motion;

FIG. 5A a frontal view of a knee joint for explaining a ligament model;

FIG. 5B a side view of a knee joint of FIG. 5A;

FIG. 6 the knee joint of FIG. 1 after a tibial cut, together with a spreading device;

FIG. 7 a knee joint comprising a femoral and a tibial implant;

FIG. 8 the knee joint of FIG. 7 with a varus stress applied to it;

FIG. 9 the knee joint of FIG. 7 with a valgus stress applied to it;

FIG. 10 an ellipse which is used as a model fir the femoral implant;

FIG. 11 a model for calculating the maximum varus angle;

FIG. 12 a surface model of a femoral implant; and

Figure 13:
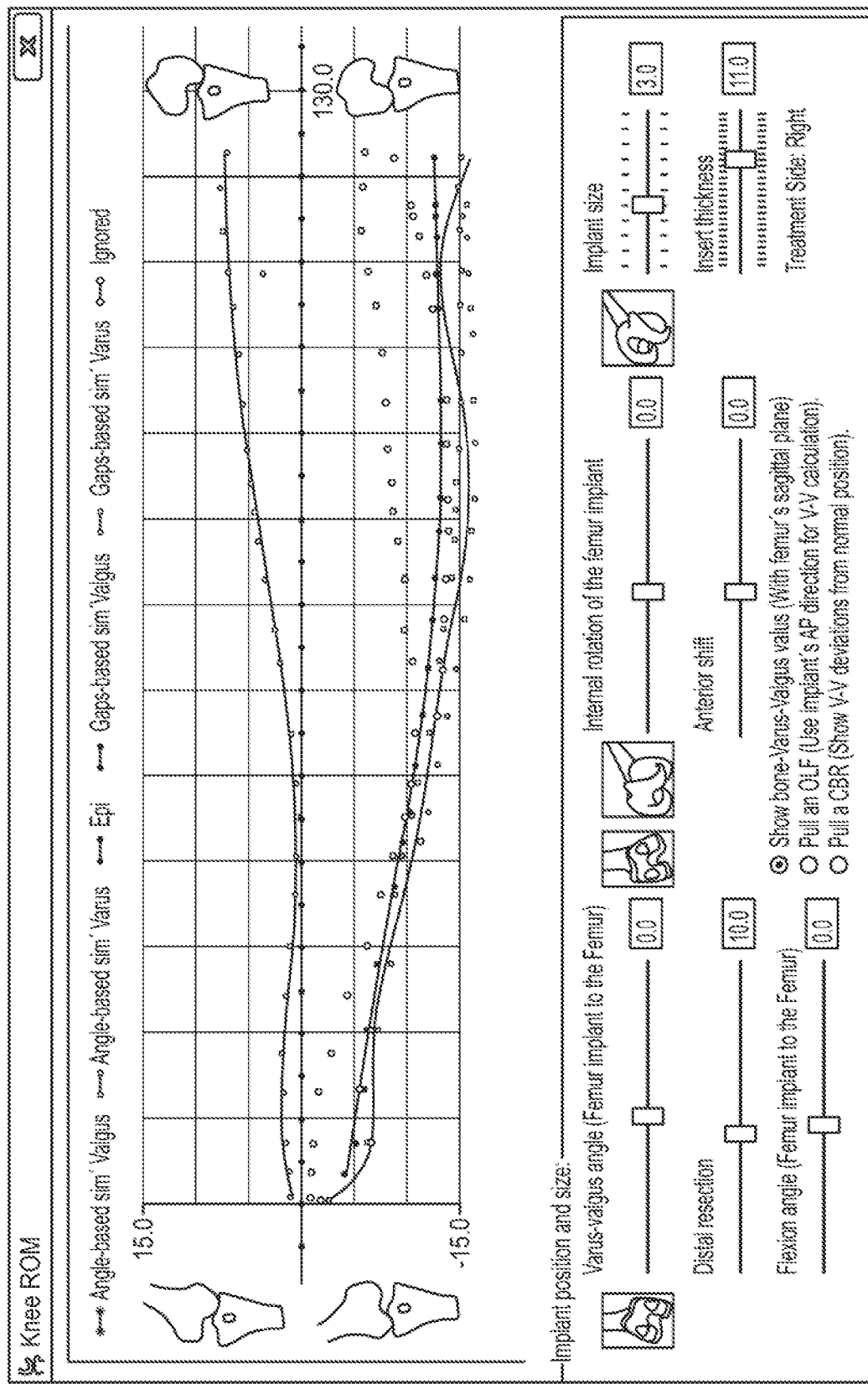

FIG. 13 a screenshot showing a calculated envelope of the range of motion.

FIG. 1 shows the basic structure of a medical navigation system 1. The medical navigation system 1 comprises a computer 2 which is connected to a display device 5, to an input device 6 and to a stereoscopic camera 7. The display device 5 is configured to display information acquired or calculated by the computer 2. The input device 6, such as a keyboard, a mouse, a trackball, a touch screen or a combination of these, is configured to receive information and provide data corresponding to the information to the computer 2. The computer 2 comprises a central processing unit (CPU) 3 and a memory 4. The CPU 3 performs the method of the present invention by processing data. The memory 4 comprises data to be processed by the central processing unit 3 and/or program code to be executed by the CPU 3. The stereoscopic camera 7 captures a three-dimensional image from which the position of a marker device, and therefore the position of an object to which the marker device is attached, can be calculated. This calculation can be performed in the camera 7, in the CPU 3 or by both in combination.

FIG. 2 shows a pre-operative knee joint between a femur 8 and a tibia 9. The femur 8 comprises a medial condyle 8a and a lateral condyle 8b. When the knee joint is bent, the femoral condyles 8a and 8h roll and/or glide on the corresponding surface of the tibia 9. The femur 8 and the tibia 9 are connected by a medial ligament 10 which connects to a feature point $F_m$ of the femur 8, namely the medial epicondyle. A lateral ligament 11 which connects the femur 8 and the tibia 9 is correspondingly connected to another feature point $F_l$ of the femur 8, namely the lateral epicondyle.

A marker device 12 is rigidly attached to the femur 8, and a marker device 13 is rigidly attached to the tibia 9. The femur 8 and tibia 9 are each registered with reference to the corresponding marker device 12 or 13, respectively, for example using a pointer (not shown). The registration data are stored in the memory 4 of the medical navigation system 1. Attaching a marker device to a bone or registering a bone to a marker device is not however part of the present invention.

In FIG. 2, the lateral condyle 8b of the femur 8 touches the surface of the tibia 9, while the medial ligament 10 is stretched to its maximum length. This relative position between the femur 8 and the tibia 9 represents a maximum valgus angle.

FIG. 3 shows the knee joint of FIG. 2, but with a varus stress applied to it. The medial condyle 8a of the femur 8 is in contact with the surface of the tibia 9, while the lateral ligament 11 is stretched to its maximum length. This relative position between the femur 8 and the tibia 9 represents the maximum varus angle. The difference between the maximum valgus angle and the maximum varus angle, with all other parameters such as internal/external rotation and flexion angle remaining unchanged, represents the range of motion of the knee joint.

The range of motion of the knee joint is preferably determined over a range of flexion angles. The envelope describing the range of motion over such a range of flexion angles can be interpolated from the maximum varus and/or valgus angles for the individual flexion angles sampled. For example, a varus stress is applied to the knee and the knee is bent over the range of flexion angles. Over this range, the medical navigation system samples the position of the marker devices 12 and 13 in order to calculate the relative position between these marker devices and therefore also between the femur 8 and the tibia 9. The maximum varus angle can be calculated for each sample, which corresponds to a particular flexion angle. A valgus stress is then correspondingly applied to the knee and the knee is bent over the range of flexion angles. A plurality of maximum valgus angles are calculated, which correspond to the plurality of flexion angles. The maximum varus and valgus angles over the range of flexion angles result in an envelope of the range of motion of the knee joint. An example of such an envelope is shown in FIG. 4. The horizontal axis represents the flexion angle, while the vertical axis represents the varus (upward) and valgus (downward) angle.

Due to the shape of the femur and the tibia, even a fully stretched ligament (a ligament stretched to its maximum length) is not completely straight but rather may comprise curved sections. In order to reduce computational complexity, the ligaments 10 and 11 are preferably considered to be straight. In addition, the maximum length of a ligament need not necessarily be defined as the maximum distance between the points at which the ligament is connected to the femur 8 and tibia 9, respectively. In this example embodiment, the length of a ligament is instead defined as the distance between the point $F_m$ or $F_l$, respectively, and a plane P which defines a tibial cut. The tibial cut can be an actual tibial cut which has been made prior to performing the present invention and which is therefore not part of the present invention, or a planned tibial cut. The ligaments 10 and 11 are considered to be perpendicular to the surface of the tibial cutting plane P. This is shown in FIGS. 5A and 5B which represent a frontal view and a side view of the knee joint, respectively.

In FIG. 5A, the maximum length of the medial ligament 10 is denoted as $D_m$ and the maximum length of the lateral ligament is denoted as $D_l$. Since the ligaments are connected to the femur and may twist for different flexion angles, the maximum length of a ligament may depend on the flexion angle. The maximum ligament lengths $D_m$ and $D_l$ are therefore also related to the index i, resulting in maximum ligament lengths $D_{m,i}$ and and $D_{l,i}$.

In this process, a plurality of relative positions between the femur 8 and the tibia 9 are sampled. Each relative position is represented by a transformation matrix wherein 0<i<N is used as an index for identifying the individual samples within the plurality of samples and wherein the matrix is preferably a 4×4 matrix. Since the femur 8 and the tibia 9 are registered to their respective marker devices 12 and 13, the positions of the points $F_m$ and $F_l$ relative to the tibia 9 are also known or can be calculated.

FIG. 6 shows an alternative approach for determining the maximum ligament lengths $D_m$ and $D_l$. After the tibial cut has been performed, a spreading device 14 is inserted between the femur 8 and the tibia 9 and adjusted to fully stretch both the medial ligament 10 and the lateral ligament 11 at the same time. The maximum lengths can then be calculated from the relative position between the femur 8 and the tibia 9. This process can likewise be performed for a particular flexion angle or also over a range of flexion angles.

FIG. 7 shows a post-operative knee joint between the femur 8, which comprises a femoral implant 8c, and the tibia 9 which comprises a tibial implant 9a. The tibial implant 9a is also referred to as an insert or tray and can have the shape of a disc. The femoral implant 8c forms the medial condyle 8a and the lateral condyle 8b. In order to reduce computational complexity, the surface of the tibial implant 9a facing the femur 8 is considered to be planar. It should be noted that this post-operative knee joint is a virtual knee joint which is simulated before arthroplasty is actually completed.

The post-operative situation assumes a particular choice for the femoral implant 8c and tibial implant 9a and a particular position of the femoral implant 8c on the femur 8 and the tibial implant 9a on the tibia 9. The purpose of the present invention is to calculate the range of motion of the post-operative artificial knee joint if these assumptions were actually implemented. In view of the calculated range of motion, it is possible to amend one or more of these assumptions until a desired range of motion results.

For each sample, the distances $D_{m,i}$ and $D_{l,i}$ are calculated using the following equations:

$$d_{m,i}=|T_i \times F_{m,i}-P|$$

$$d_{l,i}=|T_i \times F_{l,i}-P|$$

The product of the transformation matrix $T_i$ and the position. $F_{m,i}$ or $F_{l,i}$ of the feature points $F_m$ and $F_l$, respectively, transforms the corresponding point into the co-ordinate system of the tibia 9. The length of a ligament is then the shortest signed distance between this transformed point and the plane P of the tibial cut.

FIG. 8 shows a calculated relative position between the femur 8 and the tibia 9 for a virtual post-operative artificial knee joint in which the medial condyle 8a of the femur 8 (more specifically, the femoral implant 8c which is not explicitly designated in FIGS. 8 and 9) is in contact with the tibial implant 9a, and the lateral ligament 11 is stretched to its maximum length which has previously been calculated as $D_l$. This relative position represents the maximum yarns angle for the given femoral and tibial implants and the particular flexion angle. FIG. 9 correspondingly shows a relative position between the femur 8 and the tibia 9 in which the lateral condyle 11, of the femur 8 touches the tibia 9, and the medial ligament 10 is stretched to its maximum length $D_m$ for the particular flexion angle. The other parameters of the relative position, in particular the internal/external rotation, the anterior/posterior position and the lateral position are the same as those indicated by the corresponding transformation matrix $T_i$ which is used to determine both the maximum varus and maximum valgus angles.

The maximum varus and/or valgus angles are calculated for each recorded transformation matrix $T_i$. This results in a calculated, predicted post-operative envelope for the range of motion, as shown in the screenshot in FIG. 13 which is from a computer program which is running on the computer 2 and implementing the present invention. If the envelope of the range of motion is satisfactory, then the implants and the implant positions used to predict this range of motion can be implemented in actual arthroplasty, which again is not itself part of the present invention. As can be seen from the screenshot in FIG. 13, the parameters of the implants can be amended in order to predict the range of motion for different sets of parameters.

The relative positions shown in FIGS. 8 and 9 can be calculated in a number of ways. Two examples of possible approaches shall be described in more detail in the following.

In the first approach, the condyles of the femoral implant 8c are modelled as ellipses, as shown in FIGS. 10 and 11. The two ellipses representing the condyles are spaced apart by a distance $d_c$. The sizes of the ellipses and the distance $d_c$ depend on the femoral implant 8c selected.

In this first approach, the two ellipses representing the condyles 8a, 8b are first brought into contact with the surface of the tibia 9. For this purpose, the minimum distances between the two ellipses and the cutting plane P of the tibia (or the surface of the tibia in general) are calculated, as shown in the side view in FIG. 10. These two distances are then used to calculate the angle by which the femur 8, including the implant 8c, has to be rotated and the distance by which the femur 8 and the tibia 9 have to be moved translationally relative to each other in order for the two ellipses to touch the surface of the tibia 9. For this purpose, the axis of rotation and the translational direction have to be known. In one implementation example, they are calculated as follows.

The axis of rotation is defined by a vector $r_{impl}$ which is calculated as $$\vec{r}_{impl} = \vec{n}_{sp} \times (\vec{t}_{cut\_ant} \times \vec{n}_{sp})$$

where $t_{cut\_ant}$ is a vector pointing in the anterior direction of the tibia 9 and lying in the cutting plane P and $n_{sp}$ is a vector pointing to the right-hand side of the femur 8. The vector IN, is calculated as $$\vec{n}_{sp} = \vec{f}_{ant} \times \vec{f}_{mech}$$

where $F_{ant}$ is a vector pointing in the anterior direction of the femur and $f_{mech}$ is a vector corresponding to the mechanical axis of the femur. The vector $r_{impl}$ thus represents the line forming the intersection between the femoral sagittal plane and the tibial cutting plane P.

The vector $$\vec{f}_{up} = \vec{f}_{impl\_right} \times \vec{r}_{impl}$$

is then used together with the vector $$\vec{f}_{impl\_right} = M \cdot \vec{f}_{right}$$

to calculate the angle by which the femoral implant has to be rotated about the line defined by $r_{impl}$ as $$\beta = \cos^{-1}\left(\frac{\vec{f}_{up} \cdot \vec{n}_{tibia\_cut}}{|\vec{f}_{up}||\vec{n}_{tibia\_cut}|}\right).$$

The index i has been omitted from the vectors in order to improve the legibility of the formulae. The vector $f_{impl\_right}$ points to the right-hand side of the femoral implant 8c and is calculated from the vector $f_{right}$ which points to the right-hand side of the femur 8 and the transformation matrix M which represents the position of the femoral implant. 8c relative to the femur 8. The vector $n_{tibia\_cut}$ represents the normal vector to the tibial cutting plane P. A rotation matrix $R_i$ can be defined in terms of $\beta_i$ and $r_{impl,i}$ and represents the rotation needed in order to move the femur 8 into a position relative to the tibia 9 in which its condyles 8a and 8b are equally distant from the surface of the tibia 9.

The distance g by which the femur 8 has to be moved translationally relative to the tibia 9 is given by the shortest distance between the ellipse which represents the condyle and the surface of the tibia 9, as shown in FIG. 10. This is a merely two-dimensional problem. The point E on the ellipse which is nearest to the tibia 9 must have a tangent which is parallel to the surface of the tibia 9 (which is modelled as being planar). Reduced to two dimensions, this plane which defines the tibial surface becomes a line. The desired distance g is the distance between this line and the tangent to the ellipse, which is parallel to said line. The tangent can be calculated from the standard equation for an ellipse.

As can be seen from the schematic drawing in FIG. 11, the contact point of one ellipse—in this case, the medial ellipse—is fixed and used as the centre of rotation. The lateral ligament 11 and two ellipses representing the femoral implant 8c are indicated in their starting position by, continuous lines. In its starting position, the lateral ligament 11 is not fully stretched. The femur 8 is then rotated about its contact point with the tibia 9 such that the opposing ligament—in FIG. 11, the lateral ligament 11—is stretched to its maximum length. The lateral ligament 11 and the two ellipses are indicated in this position by dotted lines. The rotation is indicated by a curved arrow. The rotation moves the feature point F upwards and to the left. The angle α, which represents the maximum varus angle, is then calculated using simple trigonometric functions. This process is then repeated, with the other ellipse remaining in contact with the tibia 9 while the femur 8 is rotated until the opposing medial ligament 10 is fully stretched.

Alternatively, the condyles are not modelled as ellipses but are rather represented by the actual shape of the femoral implant, as shown in FIG. 12. In this case, a suitable mathematical description of the implant surface will most likely not be available. Instead of calculating the extent of the relative rotational and translational movement between the femur 8 and the tibia 9, an iterative approach can be applied. The relative position between the femur 8 and the tibia 9 is first altered by a translational movement along, $n_{sp}$ until one of the condyles touches the surface of the tibia 9. The femur 8 is then rotated about the contact point and the vector $r_{impl}$ until the other condyle touches the tibia. This process can be repeated if the first condyle is no longer touching the surface of the tibia after the rotation. Collision detecting techniques are preferably applied in order to detect whether or not a condyle of the femoral implant 8c is in contact with the tibia 9 (or tibial implant 9a).

In a second general approach, the two condyles of the femur 8 are not initially brought into contact with the tibia 9, as in the first approach. Instead, the feature point $F_m$ or $F_l$ at which a ligament connects to the femur 8 is used as the centre of rotation for the femur 8. The position of the point $F_m$ relative to the tibia 9 as shown in FIG. 2 is for example fixed as the centre of rotation, because the post-operative position of the point $F_m$ relative to the tibia 9 is assumed to be equal to the pre-operative relative position. The femur is then rotated about this point, about the vector $f_{impl}$ which is calculated as in the first approach, until the opposite condyle is in contact with the tibia 9. Thus, if the point $F_m$ is for example fixed as the centre of rotation, then the femur 8 is rotated about this point until the lateral condyle 8b touches the tibia 9. Whether or not the femur and the tibia are touching can be determined using known collision detecting techniques.

It should again be noted that the present invention does not comprise any surgical steps but rather merely relates to simulating the predicted outcome of an arthroplasty performed using the assumed parameters for the implant(s).

The invention claimed is:

1. A data processing method associated with a knee arthroplasty to be performed on a knee joint of a patient, the method implemented by one or more medical navigation computing devices and comprising:
   subsequent to a cut of a proximal end of a tibia of the patient and an insertion of a spreading device between a femur of the patient and the tibia, determining for one or more flexion angles of the knee joint:
   a first relative position of the tibia and the femur when the knee joint is under varus stress; and
   a second relative position of the tibia and the femur when the knee joint is under valgus stress;

determining a range of motion from the first and second relative positions;

displaying the range of motion to facilitate selection of one or more parameters associated with the knee arthroplasty;

generating, for each of the flexion angles, a first length of a lateral ligament of the knee joint and a second length of a medial ligament of the knee joint based on the first and second relative positions;

generating, for each of the flexion angles, a maximum varus angle and a maximum valgus angle for a femoral implant or a tibial implant based on the first and second lengths; and determining a range of motion envelope.

2. The method of claim 1, wherein the first relative position represents a maximum varus angle and the second relative position represents a maximum valgus angle and wherein the method further comprises determining a relative position between the femur and the tibia for each of the flexion angles.

3. The method of claim 1, further comprising generating one or more transformation matrices representing one or more of the first or second relative positions between the tibia and the femur.

4. The method of claim 1, wherein the insertion of the spreading device fully stretches the medial and lateral ligaments, wherein the resection of the proximal end of the tibia is according to a tibial cutting plane, and wherein the method further comprises measuring the first and second lengths perpendicular to the tibial cutting plane.

5. The method of claim 1, further comprising:
receiving at least one position or size parameter for a tibial implant or a femoral implant; and
modifying the range of motion based on the position or size parameter.

6. The method of claim 1, further comprising determining the first or second length based on a distance between a point on the femur and the tibial cutting plane.

7. A non-transitory computer readable medium having stored thereon instructions comprising executable code that, when executed by one or more processors, causes the one or more processors to, after an insertion of a spreading device between a femur of a knee joint of a patient and a resected surface of a tibia of the knee joint:
determine for one or more flexion angles of the knee joint:
a first relative position of the tibia and the femur when the knee joint is under varus stress and a lateral ligament of a knee joint of the patient is stretched to its maximum length; and
a second relative position of the tibia and the femur when the knee joint is under valgus stress and a medial ligament of the knee joint is stretched to its maximum length;
determine a range of motion based on a difference between the first and second relative positions; and
display the range of motion.

8. The non-transitory computer readable medium of claim 7, wherein the second relative position represents a maximum valgus angle, wherein the first relative position represents a maximum varus angle, and wherein the executable code, when executed by the one or more processors, further causes the one or more processors to determine the maximum valgus and varus angles using a surface model of the femur in which the lateral or medial condyle is modelled.

9. The non-transitory computer readable medium of claim 7, wherein the executable code, when executed by the one or more processors, further causes the one or more processors to generate a first length of the lateral ligament or a second length of the medial ligament from one or more transformation matrices.

10. The non-transitory computer readable medium of claim 9, wherein the first and second lengths are further determined in relation to a plane through the resected surface.

11. The non-transitory computer readable medium of claim 9, wherein the insertion of the spreading device stretches the medial and lateral ligaments and wherein the executable code, when executed by the one or more processors, further causes the one or more processors to measure the first and second lengths perpendicular to the tibial cutting plane.

12. The non-transitory computer readable medium of claim 7, wherein the executable code, when executed by the one or more processors, further causes the one or more processors to:
receive input to amend at least one position or size parameter for at least one of a tibial implant or a femoral implant based on the range of motion; and
output to a display device a modified range of motion based upon the received input.

13. The non-transitory computer readable medium of claim 7, wherein the executable code, when executed by the one or more processors, further causes the one or more processors to determine the range of motion further based on a position or a size of a femoral implant or a tibial implant.

14. A medical navigation device, comprising:
a display device;
a non-transitory computer-readable data storage medium comprising program instructions stored thereon; and
one or more processors connected to the non-transitory computer-readable data storage medium and configured to execute the stored program instructions to:
determine for at least one flexion angle of a knee joint of a patient:
a first relative position of a tibia of the patient and a femur of the patient when the knee joint is under varus stress and a lateral ligament of the knee joint is stretched to its maximum length; and
a second relative position of the tibia and the femur when the knee joint is under valgus stress and a medial ligament of the knee joint is stretched to its maximum length, wherein the first and second relative positions are determined after an insertion of a spreading device between the femur and a resected surface of a cutting plane of the tibia;
generate range of motion data based on a difference between the first and second relative positions; and
output to the display device the range of motion data.

15. The medical navigation device of claim 14, wherein the at least one flexion angle comprises a plurality of flexion angles and the range of motion data comprises a range of motion envelope.

16. The medical navigation device of claim 14, wherein the one or more processors are further configured to execute the stored program instructions to determine the first and second maximum lengths of the lateral and medial ligaments, respectively, perpendicular to the tibial cutting plane.

17. The medical navigation device of claim 14, wherein the one or more processors are further configured to execute the stored program instructions to output to the display device an indication of a range of motion over the at least one flexion angle along an axis in order to display the range of motion data.

18. The medical navigation device of claim 15, wherein the range of motion envelope is further based on a position of a femoral implant relative to the femur or another position of a tibial implant relative to the tibia.

19. A method, comprising:
generating a cutting plane through a proximal end of a tibia of a knee joint of a patient according to a cutting plane;
resecting through the tibial cutting plane;
inserting a spreading device between the resected proximal end of the tibia and a femur of the knee joint;
applying varus and valgus stress to the knee joint when the knee joint is at one or more flexion angles;
determining a first relative position of the tibia and the femur, and a second relative position of the tibia and the femur, during the application of the varus and valgus stress, respectively, for each knee joint flexion angle;
determining a range of motion envelope;
outputting to a display device the range of motion envelope;
generating, for each of the flexion angles, a first length of a lateral ligament of the knee joint and a second length of a medial ligament of the knee joint based on the first and second relative positions;
generating, for each of the flexion angles, a maximum varus angle and a maximum valgus angle for a femoral implant or a tibial implant based on the first and second lengths; and
determining the range of motion envelope from the maximum varus and valgus angles.

20. The method of claim 19, wherein the first relative position represents a maximum varus angle and the second relative position represents a maximum valgus angle and wherein the method further comprises determining a relative position between the femur and tibia for each of a plurality of flexion angles of the knee joint.

21. The method of claim 19, further comprising generating one or more transformation matrices representing one or more of the first or second relative positions between the tibia and the femur.

22. The method of claim 19, further comprising:
inserting the spreading device to fully stretch the medial and lateral ligaments; and
measuring the first and second lengths perpendicular to the tibial cutting plane.

23. The method of claim 19, further comprising:
receiving at least one position or size parameter for a tibial implant or a femoral implant; and
modifying the range of motion based on the position or size parameter.

24. The method of claim 19, further comprising determining the first or second length based on a distance between a point on the femur and the tibial cutting plane.

25. The method of claim 19, further comprising:
adjusting a position of one or more of a femoral implant or a tibial implant based on the range of motion, wherein the position is defined by a surgical plan generated before the resection; and
implanting the femoral or tibial implant according to the adjusted position.

\* \* \* \* \*